United States Patent [19]

Kuris

[11] 4,333,197

[45] Jun. 8, 1982

[54] ULTRASONIC TOOTHBRUSH

[76] Inventor: Arthur Kuris, 3725 Henry Hudson Pkwy., New York, N.Y. 10463

[21] Appl. No.: 155,478

[22] Filed: Jun. 2, 1980

[51] Int. Cl.³ .............................................. A46B 13/02
[52] U.S. Cl. .................................. 15/22 R; 433/119; 318/118
[58] Field of Search ............. 433/119; 15/22 R, 22 A, 15/22 B; 318/118; 128/24 A, 62 A; 51/59 SS

[56] References Cited

U.S. PATENT DOCUMENTS

| | | | |
|---|---|---|---|
| Re. 28,752 | 3/1976 | Balamuth et al. | 318/116 |
| 2,917,691 | 12/1959 | Prisco et al. | 318/118 |
| 3,058,218 | 10/1962 | Kleesattel et al. | 318/118 |
| 3,194,991 | 7/1965 | Börner et al. | 318/118 |
| 3,375,583 | 4/1968 | Blank et al. | 128/24 A |
| 3,375,820 | 4/1968 | Kuris et al. | 15/22 R |
| 3,419,776 | 12/1968 | Kleesattel et al. | 318/118 |
| 3,432,691 | 3/1969 | Shoh | 310/3.1 |
| 3,447,051 | 5/1969 | Attwood et al. | 318/127 |
| 3,488,788 | 1/1970 | Robinson | 15/22 R |
| 3,539,888 | 11/1970 | Prisco et al. | 318/116 |
| 3,544,866 | 12/1970 | McLeroy | 318/118 |
| 3,654,502 | 4/1972 | Carmona et al. | 433/119 |
| 3,689,781 | 9/1972 | Kawada | 310/8.1 |
| 3,828,770 | 8/1974 | Kuris et al. | 128/62 A |
| 3,840,932 | 10/1974 | Balamuth et al. | 15/167 R |
| 3,980,906 | 9/1976 | Kuris et al. | 310/8.1 |
| 4,192,035 | 3/1980 | Kuris | 15/22 R |

FOREIGN PATENT DOCUMENTS

| | | | |
|---|---|---|---|
| 1299056 | 6/1962 | France | 15/22 R |
| 899618 | 6/1962 | United Kingdom | 15/22 R |

Primary Examiner—Gene Mancene
Assistant Examiner—John J. Wilson
Attorney, Agent, or Firm—Martin Sachs

[57] ABSTRACT

An ultrasonic toothbrush for use in personal dental hygiene care includes an elongated handle member in the form of a hollow housing having disposed therein a low voltage coil and cooperating ferrite core which is driven at ultrasonic frequencies. Affixed to the core is a brush member adapted to be received within the human mouth and moved across tooth and gingival surfaces. The brush member has been adhesively affixed to an impedance transfer device which in turn has been adhesively affixed to the core material. The impedance transfer device insures the maximum transfer of ultrasonic energy from the core material to the brush. The ultrasonic energy driving means for the core requires a relatively low voltage and permits the coil to be sealed in the handle impervious to contamination by water.

14 Claims, 6 Drawing Figures

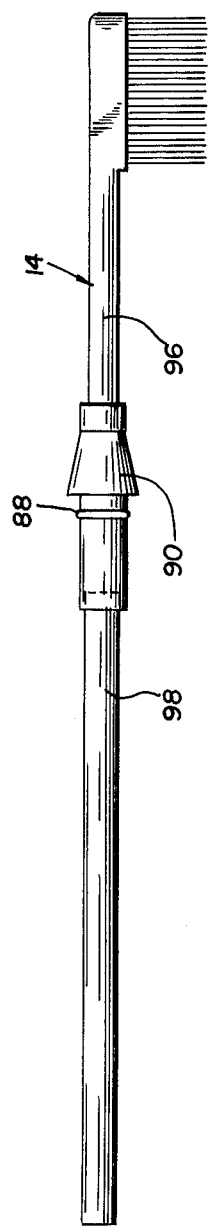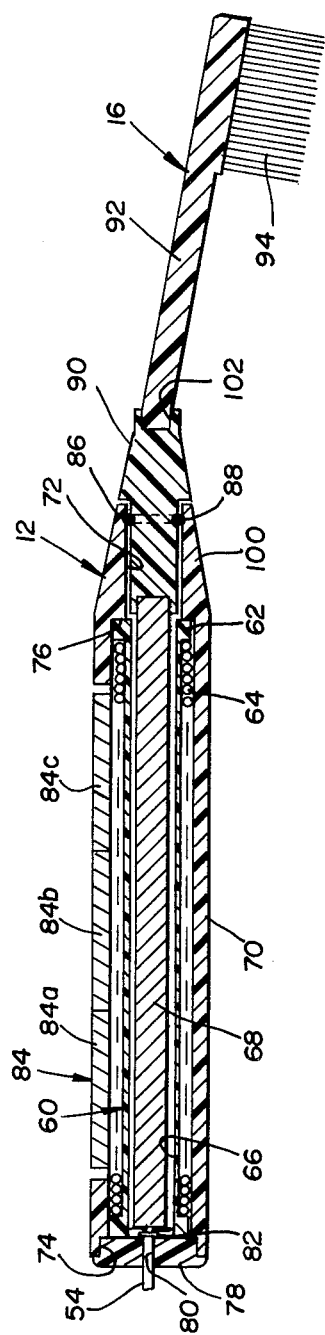

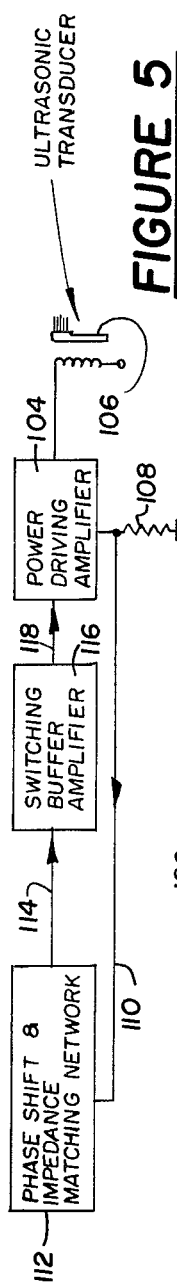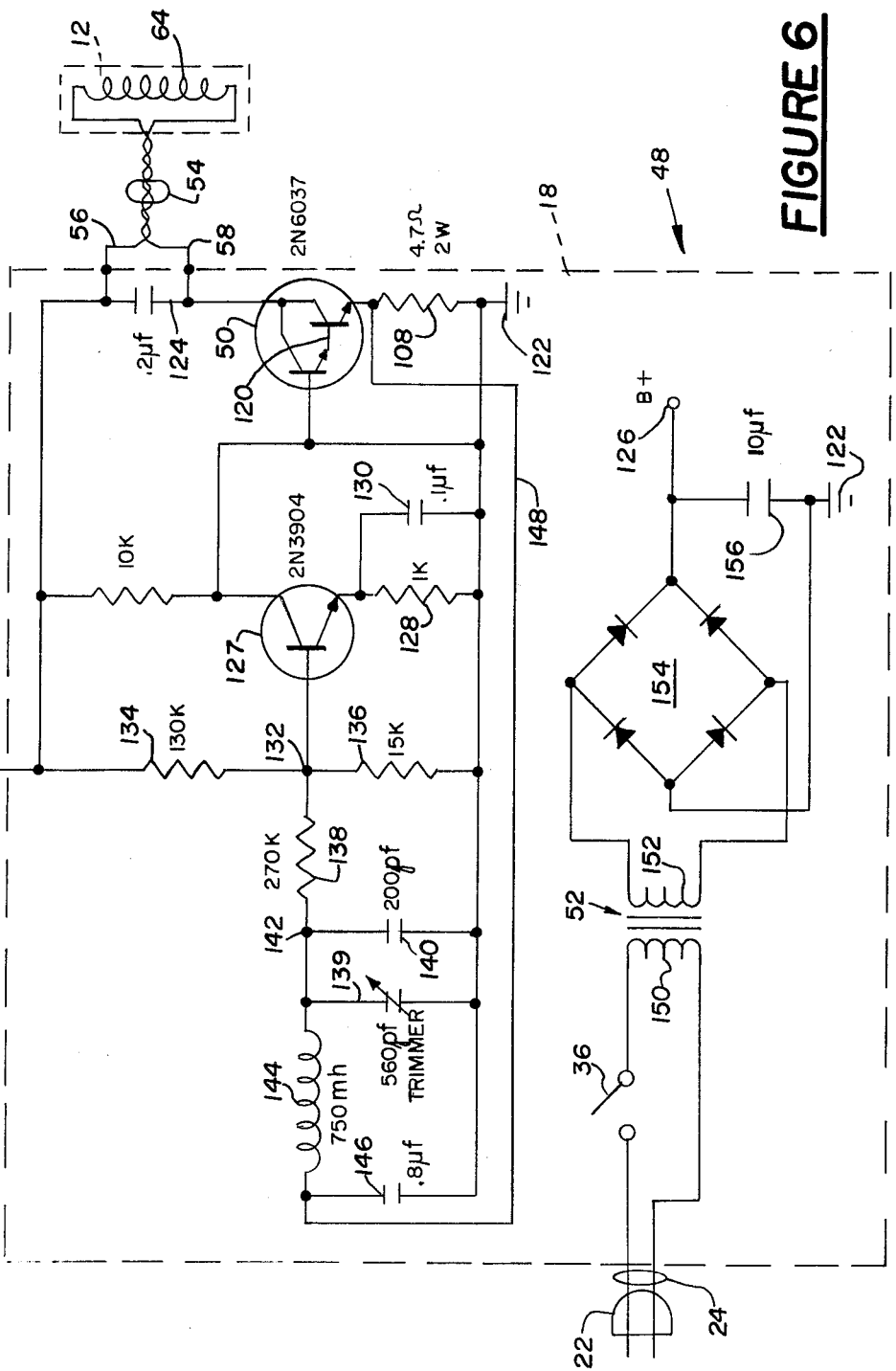

ULTRASONIC TOOTHBRUSH

BACKGROUND OF THE INVENTION

1. Field of the Invention

The present invention relates to an apparatus for oral hygiene care, and more particularly, to an apparatus for personal dental care employing ultrasonic energy suitable for regular use in the home.

2. Discussion of the Relevant Art

The art abounds with many different devices designed specifically to provide a means for dislodging food particles which may be retained between the teeth or removing deposits of plaque, tartar and scale occurring on the teeth. Many different types of manual brushing instruments have been invented over the years and finally a mechanical device which increases the number of strokes per second has become very popular with the public. However, the mechanical tooth brush has difficulty reaching the narrow space between the teeth and thus maintain the interproximal areas free of debris, or to remove foreign particles trapped at the gingival crevices i.e., the gum line. The popular motor driven tooth brushes generally operate from the standard 60 cycle (Hz) source or include a rechargeable battery which may be recharged from the 60 Hz source. The motion imparted to the mechanical brush element may be rotary, longitudinal or oscilatory, either in a longitudinal, transverse mode or combinations thereof. Generally, the brush element moves somewhere between 60 and 120 times a second.

These motor driven tooth brushes provide advantages over the conventional manual tooth brush since many more brushing strokes occur per second by the motor driven device. Therefore, for a given amount of time more brushing is performed by the user.

However, the use of these conventional motor driven tooth brushes does not necessarily overcome many of the disadvantages of manual brushing. Although a somewhat increased scrubbing action relative to the manual brushing occurs at the tooth surfaces which come into contact with the bristle ends stains of foreign deposits in the interproximal and gingival crevices or gum line areas are reached no better than by the manual instrument. Accordingly, the cause for many dental cavities and gingival disease are not removed by substitution of a convention motor driven tooth brush with a manually actuated implement.

Many attempts have been made to utilize an ultrasonic driven motor to drive a tooth brush in order to improve the cleaning efficiency and thereby reduce tooth decay. Many ultrasonic cleaning devices are at present available for use in dental offices, however, few, if any, devices are available for use by an individual for personal home dental care.

Many different circuit arrangements have been utilized to provide the ultrasonic energy necessary to activate a tooth brush. Typical of these devices is disclosed in U.S. Pat. No. 3,375,820 issued to Arthur Kuris, et al on Apr. 2, 1968. Typical circuitry is disclosed in U.S. Pat. No. 3,544,866 issued to R. B. McLeroy on Dec. 1, 1970. McLeroy disclosed solid state circuitry for driving the magnetostrictive transducer of an ultrasonic dental tool where the power output to the tool is controlled by variation of the duty cycle rather than amplitude of the ultrasonic output cycle. The signal voltage driving the ultrasonic magnetostrictive transducer is a square wave having a variable pulse width or duty cycle which square wave is amplified in the power amplifier to drive the magnetostrictive transducer. The circuitry disclosed therein is relatively expensive and does not lend itself for use in a personal hand held apparatus to be used for personal oral hygiene.

SUMMARY OF THE INVENTION

Therefore, it is an object of the present invention to provide a novel and improved ultrasonic tooth brush which is relatively inexpensive to manufacture and offers a maximum of safety to the individual using it.

It is another object of the present invention to provide an ultrasonic tooth brush which is reliable and efficient.

It is yet another object of the present invention to provide an ultrasonic tooth brush which may incorporate various removable brush elements that can be utilized by each member of the family individually.

It is yet another object of the present invention to provide a circuit arrangement to drive an ultrasonic transducer while protecting the user thereof from either mechanical or electrical hazards.

It is still another object of the present invention to provide an ultrasonic tooth brush which is powered by the conventional 60 cycle wall recepticle and will permit the portion of the apparatus in the individual's hands to be immersed in water without causing shock or other hazards.

An apparatus for the use in personal dental hygienic care according to the principle of the present invention comprises an elongated hollow housing member having disposed therein an elongated coil extending substantially the entire length thereof. A means is provided for magnetically biasing the coil by providing lines of flux within the coil prior to the coil's receiving any ultrasonic energy. A brush member, adapted to be received within the human mouth and moved across teeth and gingival surfaces includes an elongated portion of magnetostrictive core material extending from one end of the brush member and is removably received into the central part of the coil means and cooperates therewith. The brush has a plurality of bristles affixed therein and is disposed on the opposite end of the brush member. An impedance transferring means is adhesively connected between the brush member and the elongated magnetostrictive core material for transferring the ultrasonic energy therebetween. An ultrasonic energy driving means is coupled to the coil means and is connected to a source of electrical energy and provides the ultrasonic energy to the coil means for displacing the brush member at an ultrasonic rate.

The ultrasonic driving means for the ultrasonic tooth brush, according to the principles of the present invention, comprises a power driving means coupled to the core means. The power driving means provides a feedback voltage proportional to the current in the coil means at substantially the resonant frequency of the coil means and coil combination. Switching amplifier means is coupled to the power driving means and provides a square wave driving signal at substantially the resonant frequency of the coil means and coil combination. Phase shift and impedance matching means are coupled to the power driving means and the switching amplifier means for increasing the feedback voltage coupled to the switching amplifier from the power amplifier and phase shifts the feedback voltage an amount sufficient to sustain oscillations at the resonant frequency. The power driving means and the switching amplifier means are coupled to a source of DC operating voltage.

The foregoing and other objects and advantages will appear from the description to follow. In the description reference is made to the accompanying drawing which forms a part thereof, and in which is shown by way of illustration a specific embodiment in which the invention may be practiced. This embodiment will be described in sufficient detail to enable those skilled in the art to practice the invention, and it is to be understood that other embodiments may be utilized and that structural changes may be made without departing from the scope of the present invention. The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawing in which:

FIG. 3 is a cross-sectional view of the hollow housing with a typical brush member inserted therein;

FIG. 4 is a side view in elevation of another embodiment of a brush member utilizable in the hollow housing of the instant invention;

FIG. 5 is a functional block diagram of the preferred ultrasonic driving circuit arrangement; and FIG. 6 is a schematic circuit diagram suitable for driving an ultrasonic transducer such as that utilized in the preferred embodiment.

DESCRIPTION OF THE PREFERRED EMBODIMENTS

Figure 1:
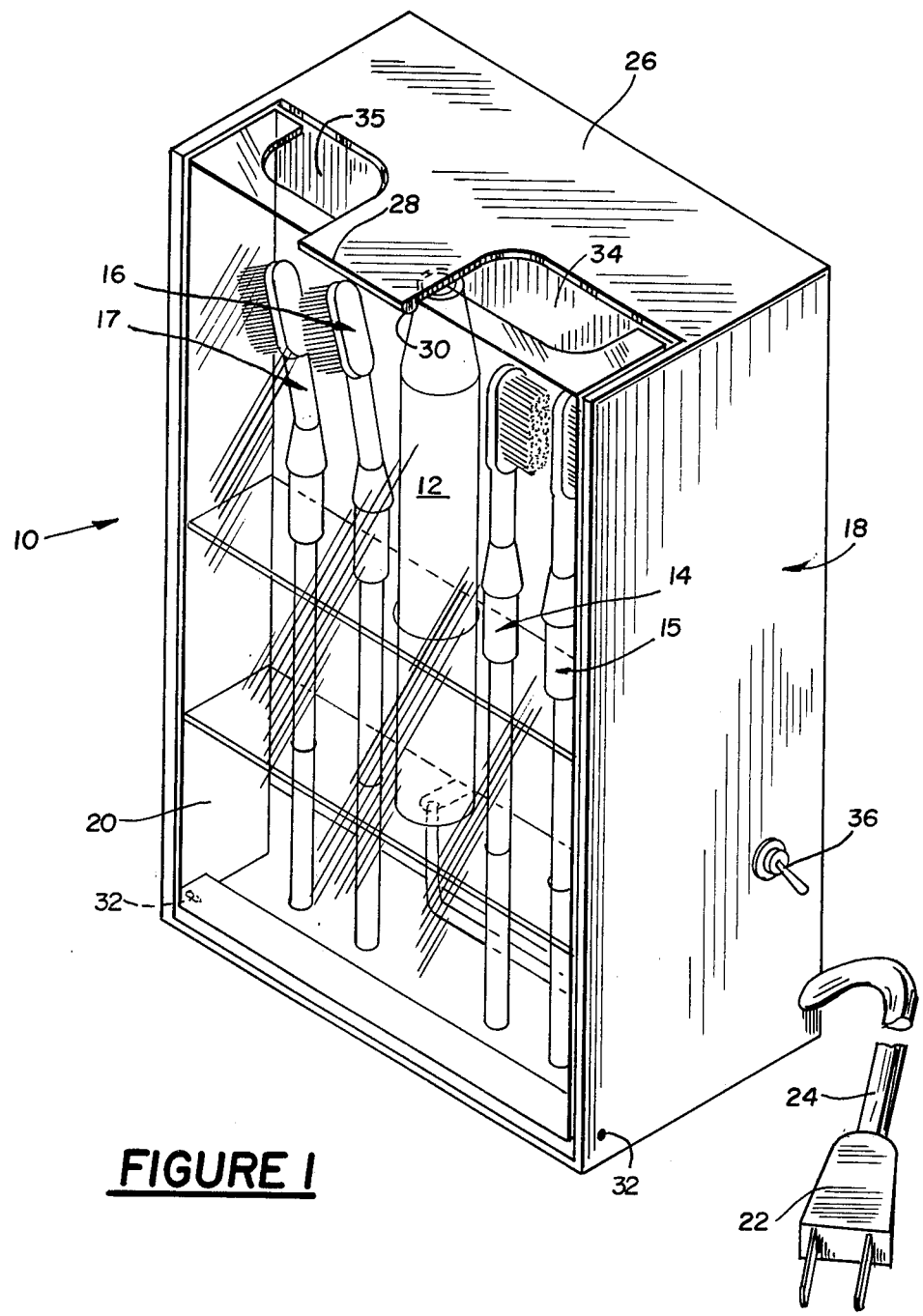
FIG. 1 is a perspective view of the ultrasonic tooth brush housing with a plurality of brush members retained in a display case, according to the principles of the present invention.

Referring now to the figures, and in particular to FIG. 1, which shows an ultrasonic tooth brush 10 that includes a housing member 12 and a plurality of brush members 14, 15, 16, and 17 mounted in a display case 18 provided with a transparent door 20. The display case 18 is adapted to be mounted on any convenient vertical surface or alternatively may be so that it stands on a convenient flat surface proximate a conventional wall receptacle, not shown, that provides 117 volts at 60 Hz. The available energy from the conventional wall receptacle is coupled into the display case 18, via a conventional plug 22 and feed wire 24. The cover 26 of the display case 18 is provided with an overhanging lip 28 having a small downwardly extending protrusion 30 provided at the distal end thereof. The door 20 is pivotally retained by the housing 18 by means of pins 32 placed at both ends of the bottom portion of the door 20.

A slight pressure on the overhanging lip 28 in the upward direction enables the door 20 to freely move away from the cover 26 of the housing 18 carrying the housing member 12 and the brush members 14 through 17 along with it making it readily accessible to be selected by the user thereof. In addition, openings 34 and 35 are provided between the door 20 and the cover 26 to permit the free movement of air therein so that any moisture accumulating on the brushes may freely evaporate into the surrounding atmosphere.

Removable feet, not shown, may be placed on the underside of the display case 18 in order to prevent it from marring a horizontal surface upon which may be placed and also to provide additional clearar... to permit the door 20 to freely open without interference with the horizontal surface. Alternatively, the pivot point may be raised above the bottom edge of the display case 18 to obviate the need for raising the display case 18 above a horizontal surface.

Figure 2:
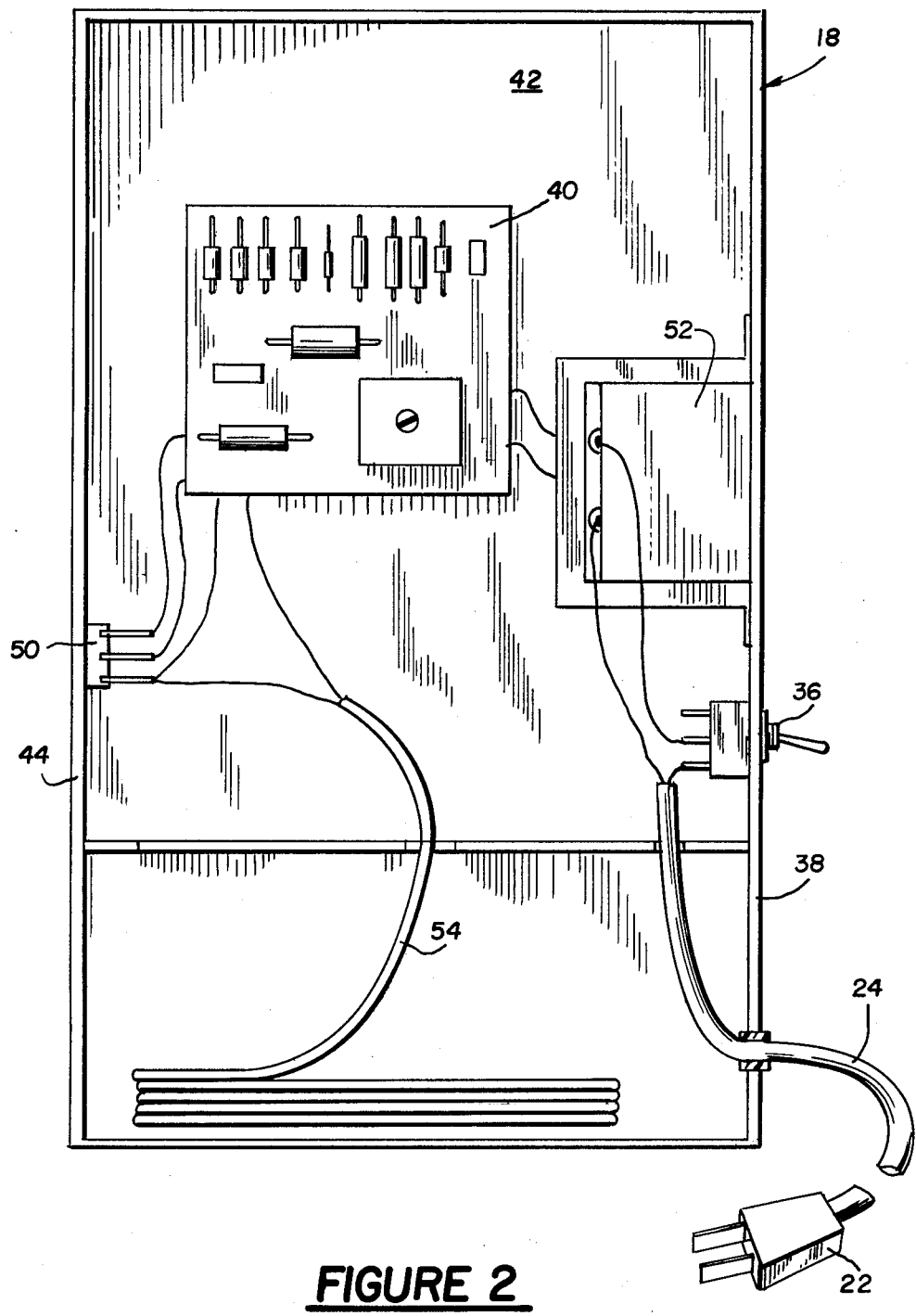
FIG. 2 is a rear view of the case shown in FIG. 1 showing the arrangement of the circuit components.

FIG. 2 is a rear view of the display case 18 which exposes the electrical components used in the preferred circuit arrangement. The preferred circuit arrangement will be disclosed hereinafter in detail. An on/off power switch 36 is incorporated in the side wall 38 of the display case 18 and functions to energize the electrical driving circuit arrangement described hereinafter.

It is contemplated that the display case 18 will be fabricated from a plastic material in a plurality of colors to compliment the decor in which it is to be used. The door 20 is preferably fabricated out of material such as lucite so that the brush members may be readily visible to the user.

The components disclosed in the preferred embodiment herein are of the discrete type including a plurality of resistors, capacitors and transistors and are preferably mounted on a printed circuit assembly board 40 to the rear inside area 42 of display case 18, in a conventional manner. The side walls 38 and 44 may be made of metal such as aluminum, permitting the power drive transistor 50 to be mounted directly to the side wall 44, in a conventional manner, so that any heat dissipated therein may be readily radiated to the external atmosphere. The input power transformer 52 is shown affixed to wall 38 and is mounted thereto, in a conventional manner, and functions to reduce the input line voltage from a conventional 117 volts AC, 60 Hz to less than 20 volts AC 60 Hz for use by the ultrasonic driving circuit arrangement 48 disclosed in detail in FIG. 6. It is to be understood that although the three components have been disclosed in the preferred embodiment, it is contemplated that a single unit comprising a large scale integrated (LSI) package may be used in production to contain all the components except the power transformer 52. The circuitry appearing on printed circuit board 40 is connected to the housing member 12, via a flexible cable member 54, which includes two lead wires 56 and 58 that are connected to transducer motor coil 60 which is rigidly mounted in the housing member 12 as will be explained hereinafter.

Referring now to FIG. 3 which is a cross-section view of the housing member 12 that functions as a handle for the brush members 14, 15, 16, and 17 which are received therein and are readily interchangeable. The transducer motor coil 60 includes a bobbin 62, preferably of plastic material such nylon or the like, upon which a plurality of insulated copper wire turns are wound, thereby forming an air core inductor having an inductance of approximately 65 microhenrys. The ends of coil 64 are connected, via wires 56 and 58 in cable 54, to the solid state ultrasonic circuitry as shown in FIG. 6. The bobbin 62 is provided with a centrally disposed bore 66 which has an internal diameter slightly larger than the core material 68 adapted to be received therein.

The housing member 12 is fabricated from a plastic or insulating material such as Lexan, or the like, and is provided with an opening 72 at one end thereof which is adapted to receive the brush member therein. The other end is provided with an opening 74, which in the preferred embodiment is slightly larger than the opening 72 and is sufficiently large to receive the transducer motor coil 60 therein. A lip or stop 76 is provided in the plastic casing 70 in order to accurately position the transducer motor coil 60. An end member 78 is provided with an aperture 80 through which the cable 54 may pass. The cable 54 is provided with a retaining device 82, of a conventional type, in order to provide a strain relief for the cable 54. Lead wires 56 and 58 of cable 54 are soldered to coil 64, in a conventional manner thereby providing a continuous circuit path. End member 78 is inserted into opening 74 and retained therein by a conventional type of adhesive. End member is preferably in intimate contact with bobbin 62 therefore urging it against the lip or stop 76 holding it in a fixed position.

In order to provide a biasing flux for the coil 64 of the transducer motor 60, a bar magnet 84 is disposed parallel to the longitudinal axis of the transducer motor coil 60. Although the bar magnet is shown to consist of three separate independent units 84a, 84b and 84c, a single bar magnet extending longitudinally along the motor coil 60 for substantially the entire length of the coil 64 and disposed externally of the core 60 may be utilized. Preferably the bar magnet 84 is adhesively retained in the casing 70 of the housing member 12.

Proximate open end 72 of plastic casing 70 an internal depression 86 circumscribing the inner diameter of the opening is provided. The depression 86 is adapted to cooperate with O-ring 88 placed at a nodal point on the impedance transfer device 90. The impedance transfer device 90 is provided with a frusto-conical portion extending towards the brushing portion 92 of brush member 16.

Brushing portion 92 has bristles 94 affixed therein in a conventional manner. As show, the longitudinal axis of the brushing portion of brush member 16 is disposed at an angle from the longitudinal axis of the core material 68. In another embodiment, as shown in FIG. 4, the brushing portion 96 is in line with the longitudinal axis of the core material 98. An impedance transferring device 90 is used to transfer the ultrasonic energy from the core material to the brushing portion 96 of the brush member 14 in the same manner as impedance transfer device 90 transfers the ultrasonic energy from core member 68 to the brushing portion 92 of brush member 16. The O-ring 88 which preferably is placed at the nodal point occurring on the impedance transfer device 90 is identical to the O-ring utilized on the impedance transfer device utilized on brush member 16. Brush members 16 and 14 are interchangeable within the housing member 12 and are utilized in accordance with an individual's personal preference.

Preferably, impedance transfer device 90 is provided with bores 100 and 102 at each end thereof. Bore 100 is adapted to receive core material 68 therein which is retained by an adhesive, in a conventional manner, and bore 102 is adapted to receive brushing portion 92 therein which is adhesively detained in a conventional manner.

Preferably, the core material utilized is a low permeability nickel-zinc ferrite which has a relatively high magnetostrictivity defined as the change in length divided by its original length, with an applied magnetic field. A suitable material is manufactured the Indiana General Corporation, Keasbey, N.J., and known as "Ferramic" Q-3. Other types of ferramics well known to those knowledgeable in the art may also be utilized to provide the necessary magnetostrictivity required for proper operation.

Preferably, the brushing portion of the brush members is fabricated from a relatively hard plastic material capable of transferring the ultrasonic energy to the bristles 94 that have been transferred, via the impedance transfer device, from the core material 68.

The transducer motor coil 60 and core 68 combination is sometimes referred to as an ultrasonic transducer of which there are many different types that operate with magnetostrictive principles.

FIG. 5 is a functional block diagram of the preferred circuit arrangement for driving an ultrasonic transducer and includes a power driving amplifier 104 which is connected to the ultrasonic transducer 106. In the present embodiment the ultrasonic transducer 106 is utilized to drive a toothbrush, however, other implements may be utilized as well.

The power driving amplifier 104 is provided with a feedback resistor to generate a feedback voltage proportional to the current flowing in the coil of the ultrasonic transducer 106. The feedback voltage is coupled, via lead 110, to a phase shift and impedance matching network 112. The phase shift and impedance matching network is connected, via lead 114, to switching buffer amplifier 116. Switching buffer amplifier 116 is connected, via a lead 118, to the power driving amplifier 104.

The components appearing in each of the functional blocks are described more specifically in FIG. 6 which discloses a preferred embodiment of the present invention and may be utilized for driving an ultrasonic transducer of the magnetostrictive type disclosed herein.

The power driving amplifier 108 includes Darlington transistor 120, which may be transistor type 2N6037. The emitter electrode of transistor 120 is coupled to a ground reference 122, via resistor 108. The collector electrode of transistor 120 is coupled, via lead wire 58, coil 64, lead wire 56, to the source of operating DC voltage (B+).

A capacitor 124 is connected across lead wires 56 and 58 and therefore is in parallel with coil 64 and forms a parallel resonant circuit therewith when the ferrite core of the brush member 12 is inserted therein. The base electrode of transistor 120 is connected to the source of operating DC voltage 126, via a 10,000 ohm resistor and is also connected to the collector electrode of transistor 127. Transistor 127 is preferably a 2N3904. Transistor 127 functions as a switching and buffer amplifier and provides the driving signal voltage for the power driving amplifier 120. The emitter electrode of transistor 127 is coupled to the ground reference 122, via the parallel combination of resistor 128 and capacitor 130. The base electrode of transistor 126 is connected to the juncture 132 of resistors 134 and 136. The other end of resistor 134 is connected to the source of operating DC voltage 126 and the other end of resistor 136 is connected to the ground reference 122. Preferably, the source of operating DC voltage is approximately 16 volts peak.

The base electrode of the transistor 127 is coupled, via a resistor 138, to a parallel combination of capacitors 139 and 140. The other end of capacitors 139 and 140 is connected to the ground reference 122. Capacitor 139 is a variable or trimmer capacitor and its function will be explained hereinafter. The juncture 142 of resistor 138 and capacitors 139 and 140 is connected to an inductor 144 which has its other end connected to ground reference 122, via a capacitor 146 and is connected, via a lead 148, to the emitter electrode of transistor 120.

The source of operating voltage, as stated earlier, is the 117 volts, 60 Hz source, which is obtained from a conventional wall receptacle. The plug 22 couples the AC voltage, via cable 24 and on/off power switch 50 to the primary 150 of transformer 152. Transformer 152 is a step-down transformer providing a voltage on its secondary 152 of approximately 12 volts RMS. A full wave diode bridge 154 rectifies the AC voltage providing a DC operating voltage between terminal 126 and ground reference 122 of approximately 16 volts peak. A capacitor 156 is connected from the DC voltage source 126 to ground reference 122 and functions to prevent ultrasonic frequency voltages from being reflected back into the source of AC voltage obtained from the receptacle.

In operation, the ferrite core is inserted into the coil 64 presenting a load thereto and raising its output inductance. The combination of coil 64 and capacitor 124 with the ferrite rod therein forms a resonant circuit at the resonant frequency fundamental of the ferrite. The ferrite core is selected so that a one-half wave length standing wave is present in order to transfer a maximum of ultrasonic energy at one end. With the material selected a four inch rod will provide a standing wave at about 26 KHz. As the frequency goes through the resonance of the rod the phase between the driving current and the driving voltage varies from $+90°$ to $-90°$, with the phase being zero at resonance. This is similar to what occurs in a conventional resonant tank circuit but, however, in the present application, the ferrite core rod provides the resonant frequency. A signal voltage appearing at the emitter of transistor 120 is in phase with the current in coil 64 and is coupled to the inductor 144, via lead 148.

The feedback voltage is coupled through the pi network consisting of capacitor 146, inductor 144 and capacitors 139 and 140 to shift the phase sufficiently to cause the circuit to oscillate and provide the proper impedance to enable coupling into the base electrode of transistor 127. The trimmer capacitor 139 is adjusted until it resonates with inductor 144 at the frequency of operation. When properly tuned between 10 and 40 volts AC is provided at the juncture 142. Coupling this voltage to the base electrode of transistor 127 causes transistor 127 to saturate and clip (cut off) the positive peaks of the sine wave and change it into a square wave. As the sine wave conducts in the opposite or negative direction, transistor 127 is turned off. Therefore, the voltage occurring at the collector electrode of transistor 127 is a square wave which is coupled to the base electrode of the power driving transistor 120 and is at the resonant frequency of the ultrasonic transducer. On the positive portions of the input voltage the current in coil 64 is at a maximum. On the negative peaks, the current in coil 64 is essentially zero and the transducer rings at its magnetostrictive frequency providing the feedback signal voltage appearing at the emitter of transistor 120 which sustains the oscillations.

In practice, the circuit requires approximately five watts of input power and is capable of delivering about three watts out. The present circuit is reliable and efficient. The circuit as disclosed requires a mininum number of components and has an efficiency which far exceeds those known in the prior art. Once the core material vibrates at an ultrasonic rate it transfers its energy via the impedance transfer device to the brushing portion of the brushing members thereby causing the bristles to vibrate in an ultrasonic manner and as is known from observation that the ultrasonically vibrating bristle clusters are accompanied by vigorous cavitational action when the cleaning area is wet. This is a direct consequence of the high peak accelerations and thus introduces a factor not present in other known tooth cleaning aids. Thus, cavitational action in the interproximal areas of the teeth would tend to remove plaque in a manner analogous to the way in which a cavitating liquid removes dirt from inaccessible machine parts.

In order to avoid undue loading of the core material, the O-ring 88 while functioning to hold the brush members in the housing member also functions to eliminate the flow of liquid into the casing 70 thereby reducing any extraneous loads on the brush members and reducing the effective efficiency of operation.

Hereinbefore has been disclosed an efficient, simple, inexpensive, ultrasonic tooth brush and circuit arrangement for driving same. It will be understood that various changes in the details, materials, arrangement of parts and operating conditions which have been herein described and illustrated in order to explain the nature of the invention may be made by those skilled in the art within the principles and scope of the present invention.

Having thus set forth the nature of the invention, what is claimed is:

1. An apparatus for use in personal dental hygienic care comprising:
    (a) an elongated hollow housing member having disposed therein;
        (i) an elongated coil means extending within said housing member, and
        (ii) magnetic biasing means disposed along the length of said coil means for providing lines of flux within said coil means;
    (b) a brush member adapted to be received within the human mouth and moved across tooth and gingival surfaces including,
        (i) an elongated portion of magnetostrictive core material extending from one end of said brush member and removably receivable into the central portion of said coil means and cooperating therewith,
        (ii) brush means having a plurality of bristles affixed therein disposed on the opposite end of said brush member
        (iii) impedance transfer means operatively connected between said brush means and said core portion for transferring ultrasonic energy therebetween; and
    (c) ultrasonic energy driving means coupled to said coil means and adapted to be connected to a source of electrical energy for providing ultrasonic energy to said coil means for displacing said brush member at an ultrasonic rate.

2. An apparatus according to claim 1 wherein said housing means further includes sealing and retaining means at one end thereof for receiving and removably retaining said brush means therein while preventing liquids from entering said housing means.

3. An apparatus according to claim 2 wherein said sealing and retaining means includes an internally disposed depression circumscribing the inner diameter of said housing proximate said one end, said depression cooperating with an O-ring member circumferentially disposed on said impedance transfer means at a node point occurring thereon.

4. An apparatus according to claim 1 wherein said elongated coil means includes a bobbin upon which said coil means is wound, said bobbin having a longitudinal core disposed therein adapted to slidably receive the magnetostrictive portion of said brush member, said core being retained in said housing.

5. An apparatus according to claim 4 wherein said housing is provided with an internally protruding lip proximate said one end and said bobbin is retained in said housing by an end member disposed at the opposite end of said housing forcing said bobbin against said lip and being fixedly retained in said hollow housing by a retaining means.

6. An apparatus according to claim 5 wherein said retaining means is an epoxy adhesive.

7. An apparatus according to claim 1 wherein said magnetic biasing means is a permanent magnet disposed externally along the length of said coil means.

8. An apparatus according to claim 7 wherein said permanent magnet means is retained in said housing.

9. An apparatus according to claim 1 wherein said magnetostrictive core member and said brush means are adhesively affixed to said impedance transfer means.

10. An apparatus according to claim 1 wherein said brush means and said impedance transfer means are fabricated of a non-magnetic material capable of transferring ultrasonic energy.

11. An apparatus according to claim 1 wherein said brush means is coaxial with the longitudinal axis of said core material.

12. An apparatus according to claim 1 wherein said brush means is disposed at an angle from the longitudinal axis of said core material.

13. An apparatus according to claim 1 wherein said magnetostrictive core material is a ferrite.

14. An apparatus for use in personal dental hygienic care comprising:
(a) an elongated hollow housing member having disposed herein;
  (i) an elongated coil means extending within said housing member, and
  (ii) magnetic biasing means disposed along the length of said coil means for providing lines of flux within said coil means;
(b) a brush member adapted to be received within the human mouth and moved across tooth and gingival surfaces including,
  (i) an elongated portion of magnetostrictive core material extending from one end of said brush member and removably receivable into the central portion of said coil means and cooperating therewith,
  (ii) brush means having a plurality of bristles affixed therein disposed on the opposite end of said brush member, and
  (iii) impedance transfer means operatively connected between said brush means and said core portion for transferring ultrasonic energy therebetween;
(c) ultrasonic energy driving means coupled to said coil means and adapted to be connected to a source of electrical energy for providing ultrasonic energy to said coil means for displacing said brush member at an ultrasonic rate, said ultrasonic driving means including;
  (i) power driving means coupled to said core means, said power driving means providing a feedback voltage proportional to the current in said coil means at substantially the resonant frequency of said coil means and core combination,
  (ii) switching amplifier means coupled to said power driving means, said switching amplifier means providing a square wave driving signal at substantially the resonant frequency of said coil means and core combination, and
  (iii) phase shift and impedance matching means coupled to said power driving means and said switching amplifier means for increasing said feedback voltage coupled to said switching amplifier from said power amplifier and phase shifting said feedback voltage an amount sufficient to sustain oscillations at said resonant frequency.

* * * * *